(12) United States Patent
McAllen, III et al.

(10) Patent No.: US 6,319,258 B1
(45) Date of Patent: Nov. 20, 2001

(54) ABSORBABLE RIVET/PIN APPLIER FOR USE IN SURGICAL PROCEDURES

(75) Inventors: John McAllen, III, Point Pleasant; David W. Overaker, Annandale; Kevin L. Cooper, Warren, all of NJ (US)

(73) Assignee: Ethicon, Inc., Somerville, NJ (US)

( * ) Notice: Subject to any disclaimer, the term of this patent is extended or adjusted under 35 U.S.C. 154(b) by 0 days.

(21) Appl. No.: 09/408,249

(22) Filed: Sep. 29, 1999

(51) Int. Cl.[7] .................................................. A61B 17/56
(52) U.S. Cl. ...................... 606/104; 606/142; 227/175.1
(58) Field of Search ........................... 227/15–16, 26–27, 227/35–40, 48–53, 120, 132–136, 175, 176.1, 177.1, 179.1, 181.1, 901; 124/16, 26–27, 45, 50, 52, 83; 604/61–63, 71; 606/72, 117, 104, 142

(56) References Cited

U.S. PATENT DOCUMENTS

| | | |
|---|---|---|
| 4,011,602 | 3/1977 | Rybicki . |
| 4,414,967 | 11/1983 | Shapir . |
| 4,535,925 | 8/1985 | Ramey et al. . |
| 4,590,928 | 5/1986 | Hunt et al. . |
| 4,738,255 | 4/1988 | Goble et al. . |
| 4,958,510 | * 9/1990 | Denham et al. .................... 72/391.4 |
| 5,102,421 | 4/1992 | Anspach, Jr. et al. . |
| 5,135,493 | * 8/1992 | Peschke ................................ 604/64 |
| 5,167,665 | 12/1992 | McKinney . |
| 5,268,001 | 12/1993 | Nicholson . |
| 5,326,205 | 7/1994 | Anspach, Jr. et al. . |
| 5,480,403 | 1/1996 | Lee et al. . |
| 5,489,210 | 2/1996 | Hanosh . |
| 5,501,695 | 3/1996 | Anspach, Jr. et al. . |
| 5,713,903 | 2/1998 | Sander et al. . |
| 5,720,753 | 2/1998 | Sander et al. . |
| 5,725,529 | 3/1998 | Nicholson et al. . |
| 5,782,865 | 7/1998 | Grotz . |
| 5,928,244 | 7/1999 | Tovey et al. . |

FOREIGN PATENT DOCUMENTS

| | | | |
|---|---|---|---|
| 2206055A | * | 12/1988 | (GB) . |
| WO 99/26544 A1 | | 6/1999 | (WO) . |

* cited by examiner

*Primary Examiner*—Kennedy Schaetzle
*Assistant Examiner*—Kristen L. Droesch (57) ABSTRACT

This invention describes a rivet applier and rivet clip for delivering orthopedic fasteners into a patient. The rivet applier inserts the rivet body then drives a pin into the rivet body to fix the rivet in position. The device comprises a body with a handle, trigger and applier barrel. The rivet applier contains a loader and firing pin to advance and deploy rivets. The applier barrel of the rivet applier is attached to a rivet clip into which rivets may be loaded. The rivets are contained in the body of the rivet clip and loaded into the barrel of the rivet clip through a chamber. The loader of the rivet applier advances the rivet to the end of the barrel. The firing pin advances the rivet body into final position and inserts the rivet pin into the rivet.

10 Claims, 7 Drawing Sheets

ABSORBABLE RIVET/PIN APPLIER FOR USE IN SURGICAL PROCEDURES

FIELD OF THE INVENTION

The field of art to which this invention relates is surgical instruments, in particular an applier for delivering an absorbable orthopaedic fastener. Specifically, a multi-shot rivet applier that drives an absorbable polymer rivet and pin for fixating a plate to bone, especially hard tissue of the cranium or face, for plastic or reconstructive surgical procedures.

BACKGROUND OF THE INVENTION

There are currently a variety of metallic fasteners and appliers or drivers to deliver the fastener for attaching bone plates to fracture and surgery repair sites; spinal, cranial, and maxillo-facial plates have all been fastened using metal screws. The disadvantage of metal screws and other fasteners is that they are permanent and may need to be removed through a second surgical procedure. If they remain in the body, tissue atrophy and subsequent loosening of the device may occur. In addition, metallic and especially plastic screws, including absorbable polymer screws, quite often require tapping threads into the bone; a laborious task that slows the surgical procedure and can lead to poor fixation from stripping of the threaded bone.

Metallic wire or suture can be used to attach plates to bone. This technique requires a tedious method of drilling numerous holes, guiding the wire through the holes, tying and bending the wire and then cutting excess wire away to prevent irritation of soft tissues.

Furthermore, several rivet patents relate to devices which are inserted into a hole and then deployed by driving a member upwards, or proximally, through or into a radially flexible portion of the device. This requires that the hole be deeper than the depth of the deployed device in order to leave enough room to fully insert the device with some type of driver before deployment. Such designs are undesirable for surgical applications where only a thin layer of bone is available for attachment or it is not possible to drill beyond the depth of the thin bone layer for fear of damaging underlying soft tissues, such as in cranial and maxillo-facial surgical procedures. In such cases, the required length of the fastener for adequate fastening strength is very close to the total thickness of the bone.

U.S. Pat. No. 4,590,928 describes an anchor consisting of an elongated cylindrical body with a tapered coaxial channel and radially flexible legs and a pin insertable into the end having the head, the proximal end. The body is placed into a hole formed in bone and the pin is inserted into the channel to expand the legs radially into the surrounding bone. The body and pin are of biocompatible material and the body contains carbon fibers embedded in and extending longitudinally along its interior. Since carbon fibers are not absorbed by or resorbed within the body, this fastener is only partially absorbable.

This patent U.S. Pat. No. 4,590,928, describes a fastener having a solid pin. It is well known that the material properties, such as Young'modulus of elasticity and the material yield stress, of bone tissue change significantly with age and vary significantly among individuals of the same age and sex. Having a solid pin therefore limits the fastening ability of the device since the pin cannot deform if the surrounding bone is stiff that the legs cannot expand radially outwards.

In such a case where the surrounding bone is stiffer than that for which the device was designed and the pin is solid, the large force required to drive the rigid pin into the tapered hole will be such that either the legs will be deformed and rendered useless or the pin will be crushed. A radially compressible or flexible pin that could deform radially inwards to fit the internal passage under high insertion load conditions would give the fastener better performance over a wider range of bone material properties.

U.S. Pat. No. 5,268,001 describes an apparatus for emplacement of a single bone fastener in a bone. The apparatus consists of holder for holding an expandable sleeve in position within a pre-drilled hole in bone. A plunger moveable in relation to the holder forces a pin into the bore of the expandable sleeve. An attached means for separating the expandable sleeve from the holder (i.e. annular cutter) then cuts the expandable sleeve, thereby releasing the sleeve from the holder. Typical procedures require more than one fastener and varying amounts of application force. This apparatus lacks the ability to apply multiple fasteners and to change the level of force required to embed the pins into the above-mentioned expandable sleeve.

Therefore, what is needed in the art is a novel absorbable fastener for cranial, maxillo-facial, and other reconstructive surgical applications in which the fastener is inserted into a hole having the same depth as the fastener and is deployed by driving a radially compressible member downwards, or distally, into a flexible body of the fastener from above. The current invention discloses an applier for such a device wherein the applier can fire multiple rivet fasteners with little force thereby speeding and simplifying the procedure. The multiple applier consists of a cartridge, which will contain multiple rivet fasteners. The cartridge utilizes a loading mechanism which loads single rivets. The applier also consists of a firing mechanism that can produce varying degrees of force required for different surgical applications.

SUMMARY OF THE INVENTION

We have discovered a rivet applier comprising a housing with a horizontal axis, an applier barrel, a passage substantially parallel to the horizontal axis and a trigger. The applier barrel having a central chamber with a proximal chamber opening, a distal chamber opening and a slot. The proximal end of the applier barrel is attached to the housing and aligned with the horizontal axis of the applier barrel. A loader is slidably mounted within the central chamber of the applier barrel having a loader handle attached thereto and extending substantially perpendicular to the horizontal axis. A firing pin extends through said housing and the central chamber of the applier barrel. The firing pin is biased to extend through the applier barrel to the proximal chamber opening, the firing pin extending through the proximal chamber into the housing. The firing pin is mechanically linked to a trigger mechanism for restraining the firing pin in a first position and being capable of releasing the firing pin in cooperation with the movement of the trigger to allow the firing pin to move to a second position.

We have also discovered a rivet clip assembly, which is composed of a clip barrel and clip body. The clip barrel has a barrel opening on its distal end and a barrel groove adjacent to the proximal end. The clip body is attached to the barrel and extends substantially perpendicular thereto. The clip body is adapted to contain at least one rivet (and preferably a plurality), which is supported by a clip guide and biased by a clip spring. The rivet enters the barrel through a clip slot. The forward movement of the loader moves the rivets from the chamber of the clip barrel to the end of the clip barrel prior to placement in the patient. Firing the trigger advances the rivet out of the rivet applier and pushes the rivet pin into the rivet thereby securing the rivet in the patient.

DETAILED DESCRIPTION OF THE INVENTION

Figure 1:
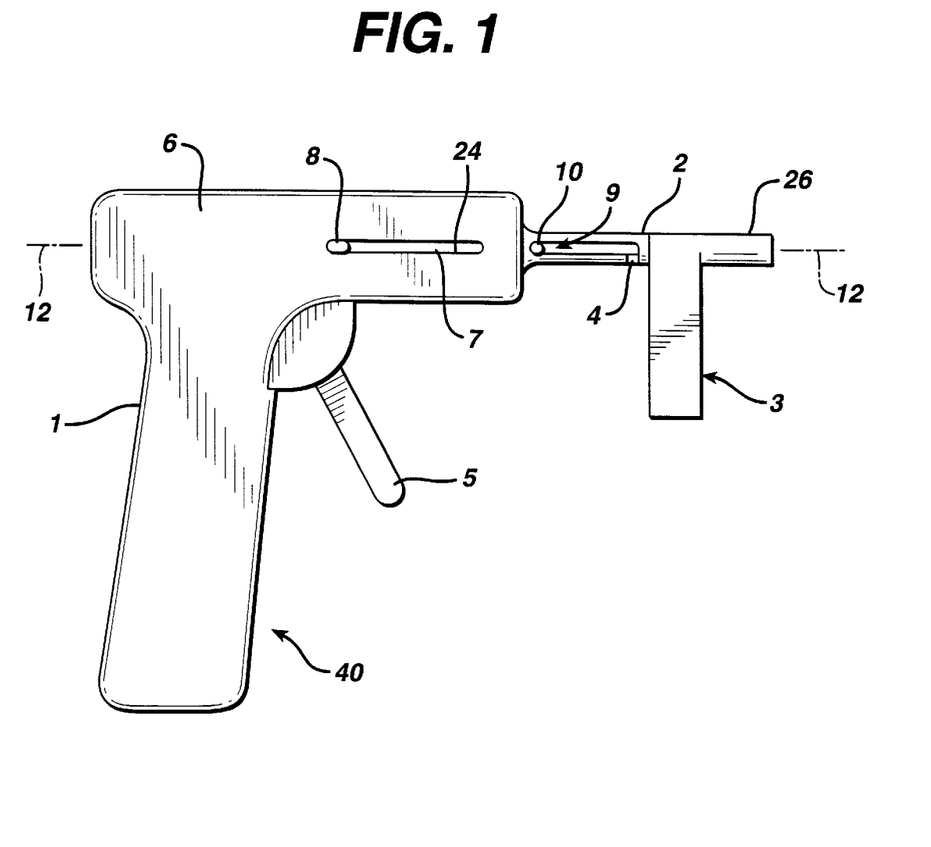
FIG. 1 is a perspective view of one embodiment of a rivet applier.
Figure 2:
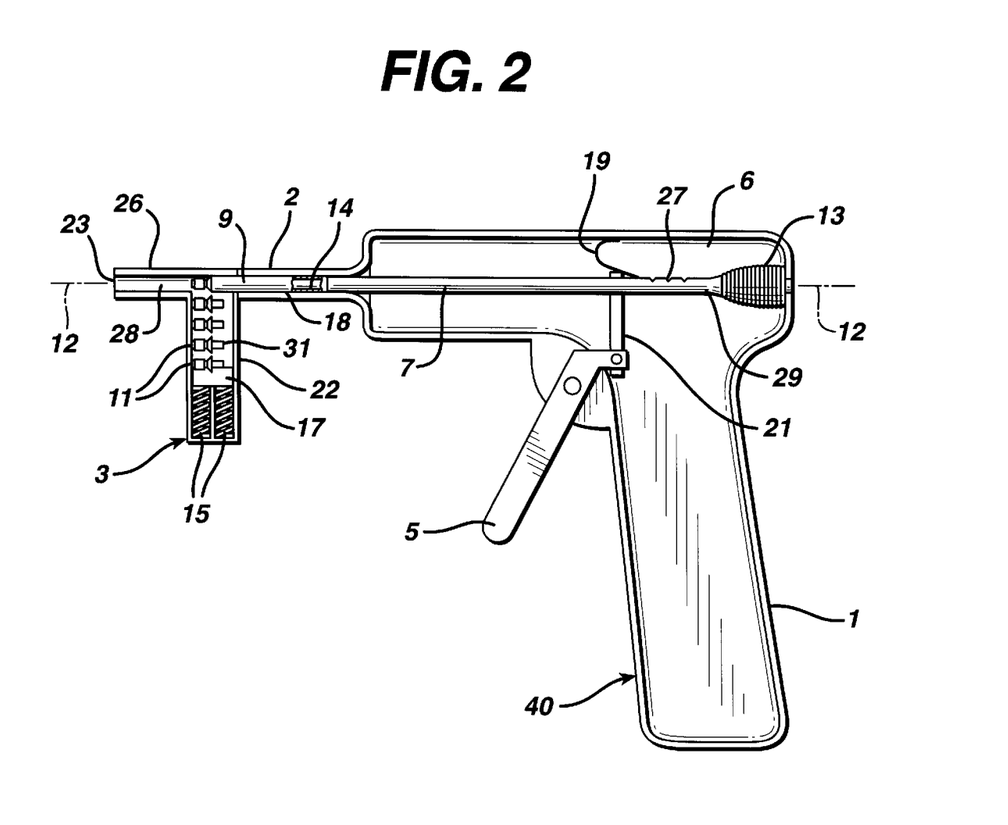
FIG. 2 is a cut away view of the rivet applier along line X—X.

The present invention discloses a multi-shot rivet applier 40 comprised of a housing 6 having a horizontal axis 12 (optionally with a handle 1 portion) and a applier barrel 2, which is illustrated in FIGS. 1 and 2. The housing 6 contains a firing mechanism that is comprised of a trigger 5, slider 21, trigger spring 19, firing spring 13, firing pin 7 and a loader 9. A rivet clip assembly 3 is releasably attached to the applier barrel 2. The rivet clip 3 is illustrated FIG. 3 and is comprised of clip barrel 26 and clip body 22.

FIG. 1 illustrates one embodiment of the present invention. In FIG. 1 the housing 6 is attached to the rivet clip 3 at the distal end 20 (shown in FIG. 6) of the applier barrel 2. The applier barrel 2 is aligned with the horizontal axis 12 of the housing 6 and has a passage 18 that is substantially aligned with the horizontal axis 12. A loader 9 (sleeve) is co-axially seated inside passage 18 of the applier barrel 2. The loader 9 has a central passage 14 (shown in FIG. 3). A firing pin 7 is co-axially seated inside the central passage 14 of the loader 9 (sleeve). The firing pin 7 is biased by a firing spring 13 contained in housing 6 which is shown to be compressed FIG. 2. FIG. 2 shows the firing pin 7 in the cocked position held back in a cocked (first) position by the trigger spring 19. The firing pin 7 is released when the trigger spring 19 is depressed by the slider 21 and is actuated when the trigger 5 is engaged. FIG. 1 and FIG. 2 show the rivet applier 40 before loading the rivet 11 into the clip barrel chamber 28. FIG. 4 is a cross-section that illustrates the relative positions of the clip barrel 26, loader 9, firing pin 7 when the rivet 11 is being deployed. As is illustrated in FIG. 4 the rivet applier 40 maybe used to drive a rivet 11 (preferably absorbable) into a bone to secure bone plate 42, for plastic or reconstructive surgical procedures FIG. 2 shows the inner components of the rivet applier 40 in the "unloaded position". The rivet applier 40 is loaded by pushing the loader handle 10 (illustrated in FIG. 1) of the loader 9 to advance the rivet 11 forward in the clip barrel chamber 28 toward the barrel opening 23. The loader handle 10 is then rotated into the locked position of the slot 4 (illustrated in FIG. 1) and prevents the loader 9 from moving backwards, away from the barrel opening 23 during firing. The loader 9 prevents any further rivets 11 from being loaded into the clip barrel chamber 28 when it is in the forward position. There is a interference fit between the rivet head 25 and the barrel opening 23 which hold the rivet 11 in place as shown in FIG. 5.

The firing pin 7 may be cocked by using the loader handle 10 or in an alternative embodiment by using firing pin handle 8. The firing pin handle 8 as seen in FIG. 1 is attached to the firing pin 7 and extends substantially perpendicularly therefrom through slot 24 in housing 6. FIG. 1 illustrates the firing pin handle 8 in the cocked position. The firing pin 7 may be cocked by moving the loader handle 10 or the firing pin handle 8 toward the back of the handle 1. As the loader handle 10 or firing pin handle 8 is moved back towards the handle of the rivet applier, the firing spring 13 is compressed and the firing pin notches 27 are engaged to the trigger spring 19.

Figure 5:
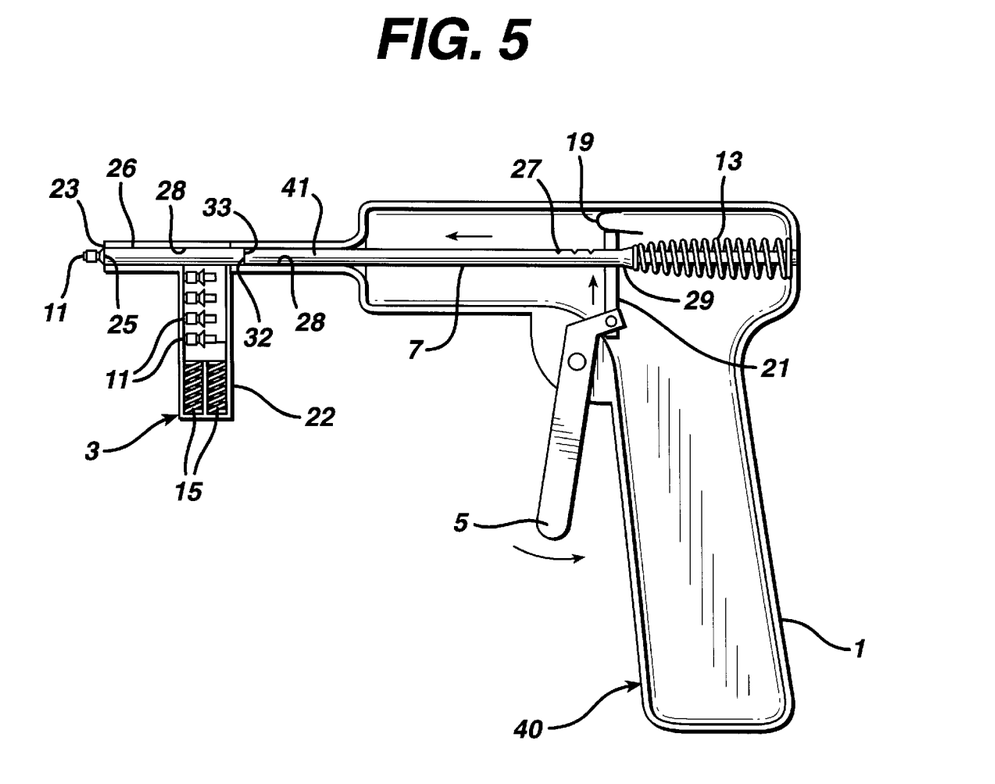
FIG. 5 is a perspective view of one embodiment of the rivet clip applier of the present invention illustrating the position of the rivet before firing of the rivet applier.
Figure 6:
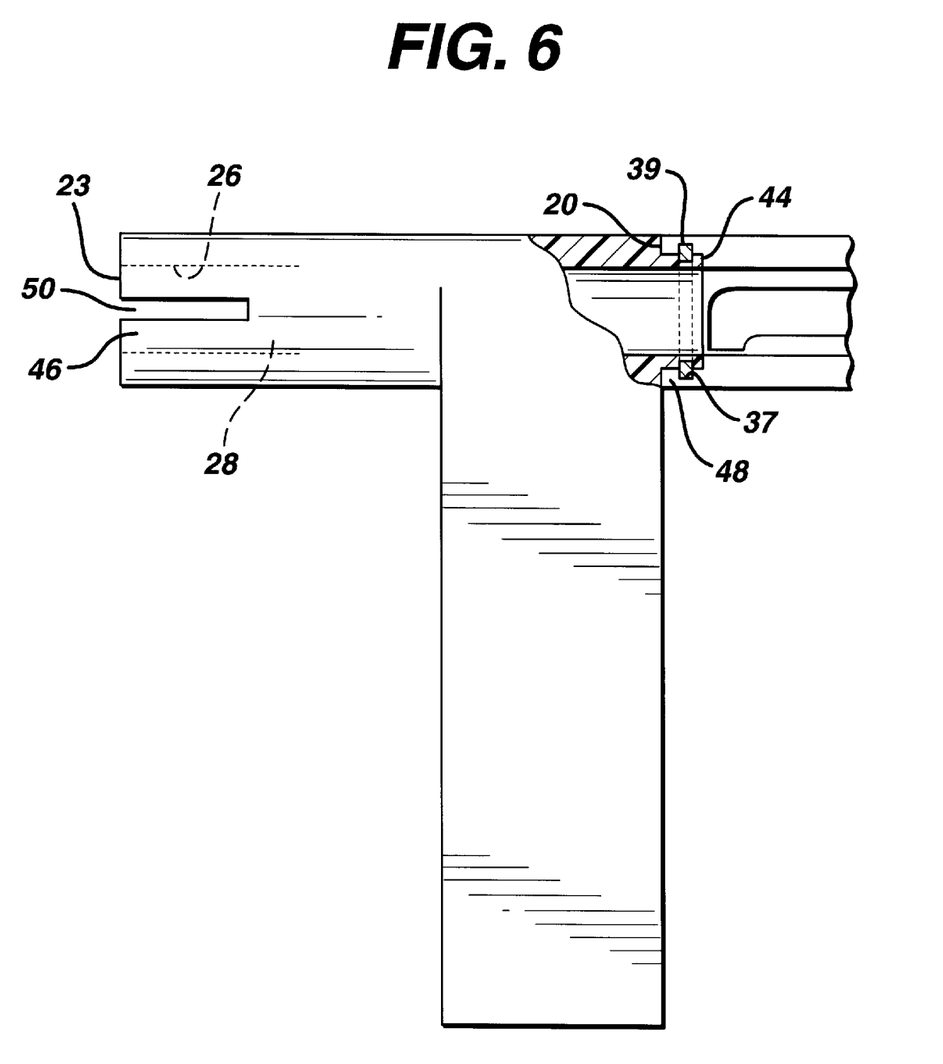
FIG. 6 is a perspective view of one embodiment of the rivet clip of the present invention illustrating various aspects of the rivet clip in a cut away view.
Figure 7:
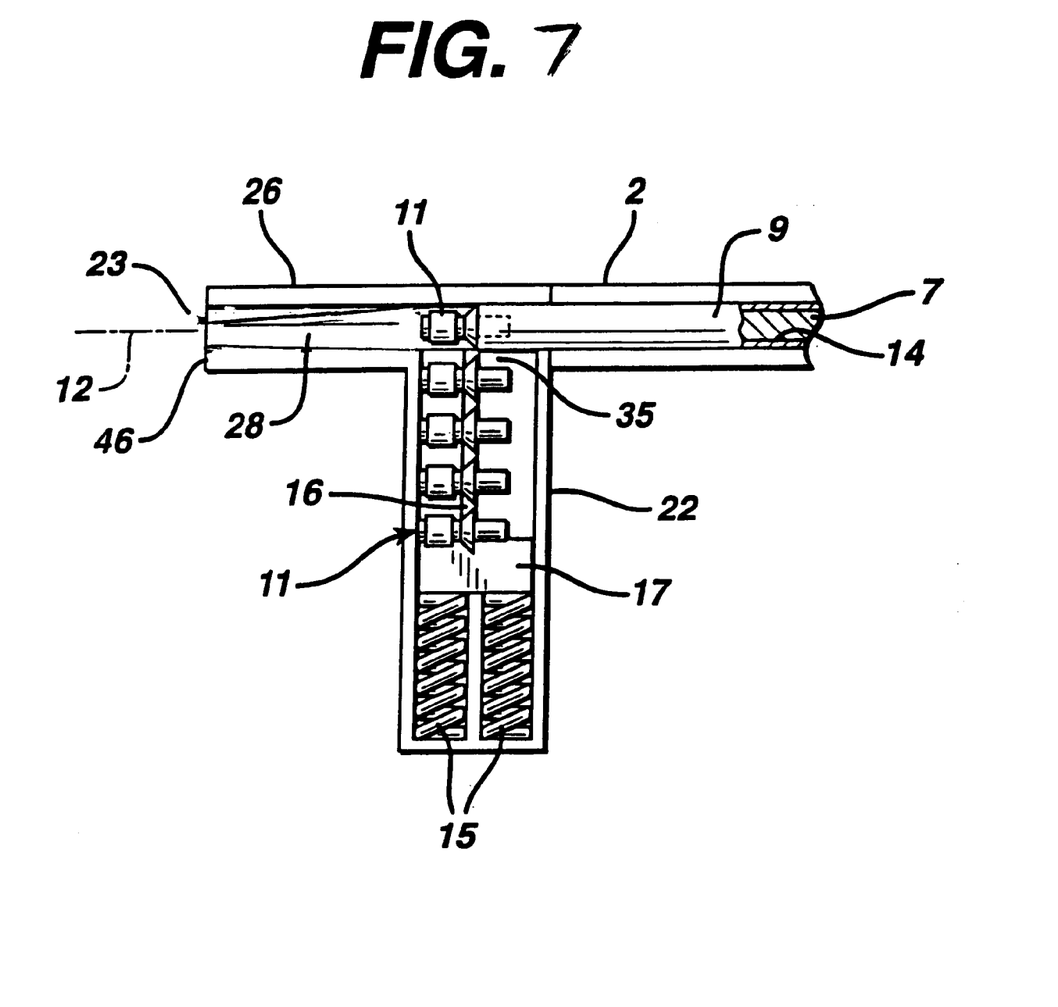
FIG. 7 is a perspective view of one embodiment of the rivet clip of the present invention.

As illustrated in FIG. 5 the rivet applier 40 is fired when the trigger 5 is pulled, actuating the slider 21, which in turn removes the trigger spring 19 from its engagement with the firing pin notches 27. The firing spring 13 exerts a force on the firing pin 7 and the firing pin 7 drives the rivet pin 31 into the rivet body. The firing pin ceases advancing when the firing pin stop 32 encounters the loader stop 33. Additional firing shots can be taken without loading a new rivet by recocking the firing pin using the firing pin handle 8 (shown in FIG. 1) and pulling the trigger 5.

The device is reloaded when the loader handle 10 is rotated out of the locked position of the barrel slot 4 and pulled back to the loading position. The loader 9 is pulled back so that the clip slot 35 is unobstructed allowing a rivet 11 to enter the clip barrel chamber 28. The rivet 11 is inserted by the clip guide 17, which is powered by clip springs 15 and guided by the clip guide rails 16. The loader 9 is moved forward to load the rivet 11 into the barrel opening 23. The same loading steps apply as mentioned previously.

Figure 3:
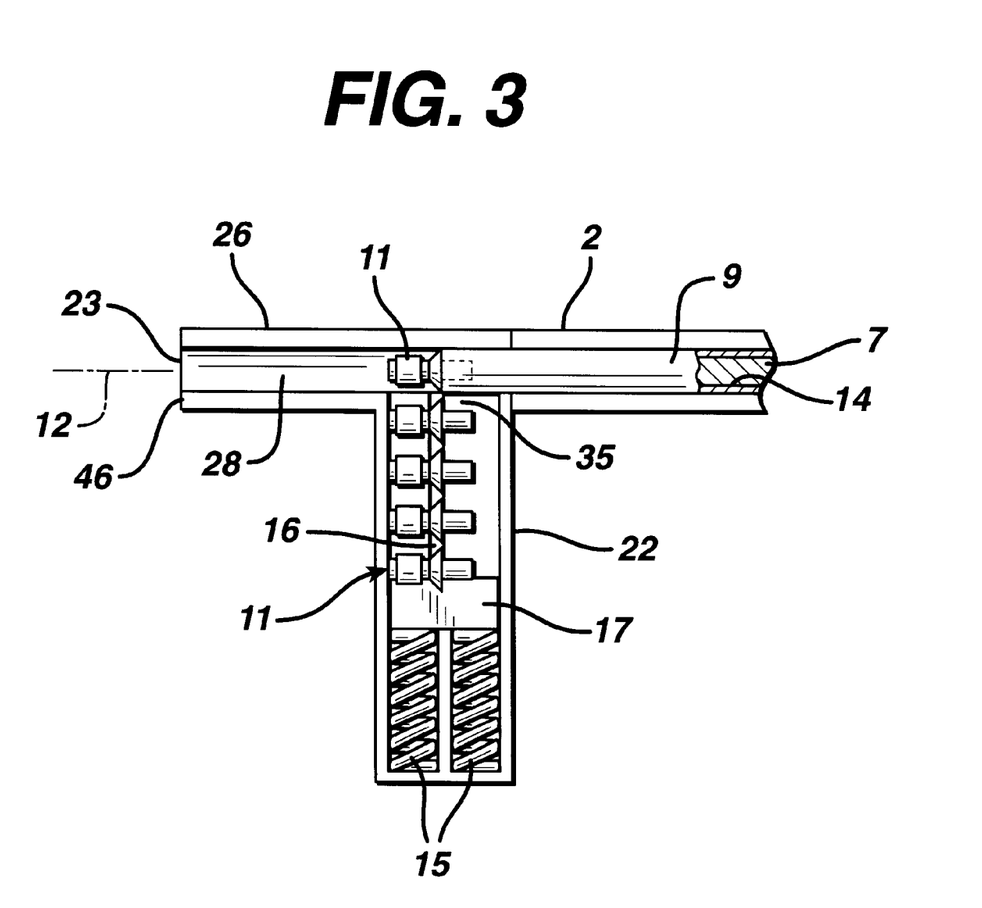
FIG. 3 is a perspective view of one embodiment of the rivet clip of the present invention.
Figure 4:
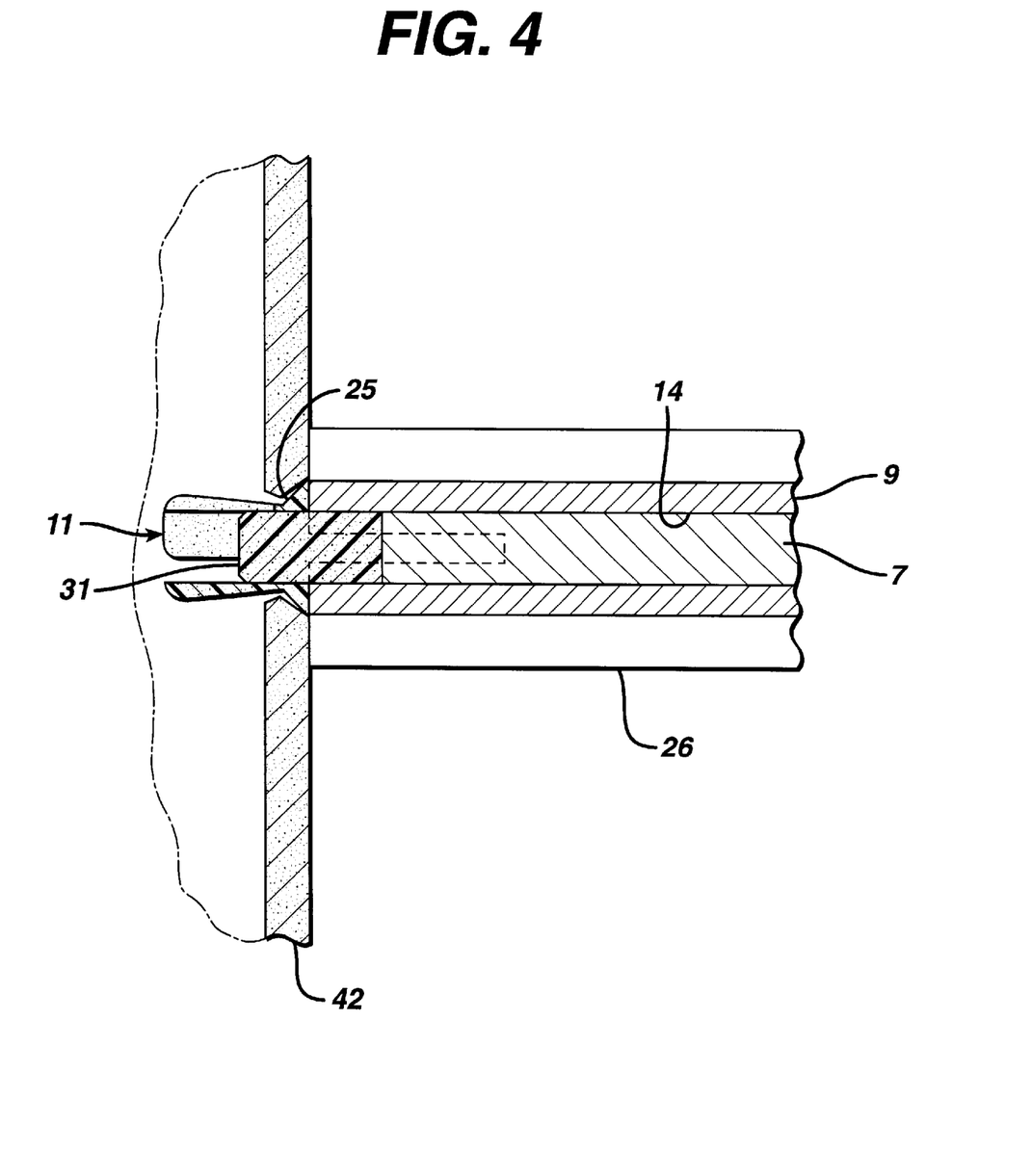
FIG. 4 is a cross-sectional view of the barrel of the rivet clip in deploying a rivet into a plate.

The rivet clip assembly 3 as illustrated in FIG. 3 is composed of a clip body 22 and a clip barrel 26. The clip body 22 is adapted to contain one or more rivets 11. The rivets are aligned in the clip body 22 by clip guide rails 16 and supported by clip guide 17 which is biased by clip springs 15. The rivets 11 enter the clip barrel chamber 28 through clip slot 35. The clip barrel chamber 28 optionally may taper toward the distal end 46 to facilitate the retention of rivets 11 in the barrel. The distal end of the clip barrel 26 may also have one or more relief cuts 50 to facilitate the controlled release of the rivets 11 during the firing of the clip applier 40. The rivets 11 are advanced to the distal end 46 (see FIG. 6) of the clip barrel 26 and ejected during the firing of the rivet applier 40. The proximal end 44 of the clip barrel 26 has adjacent thereto a raised clip ring 39 to mate with the barrel groove 37 of the applier barrel 2. This allows the rivet clip assembly 3 to be removed and replaced on the rivet applier 40. The radial snap fit junction illustrated allows the clip to rotate 360 degrees. As illustrated the diameter of the clip barrel 26 will be smaller than the inner diameter of the distal chamber opening 48 of the applier barrel 2 to facilitate a snap fit.

We claim:

1. A rivet applier comprising
    a housing with a horizontal axis, an applier barrel comprising a passage substantially aligned with the horizontal axis, and a firing mechanism comprising a trigger;
    the applier barrel having a proximal opening, a distal opening and a slot, wherein the proximal end of the applier barrel is attached to the housing and aligned with the horizontal axis of the housing;

a loader which is slidably mounted within the passage of the applier barrel, the loader comprising a loader handle attached thereto and extending substantially perpendicular to the horizontal axis and a central passage;

a firing pin which extends through said housing and the central passage of the loader, the firing pin being biased to extend through the applier barrel to the proximal opening and being mechanically linked to the firing mechanism for restraining the firing pin in a first position and being capable of releasing the firing pin in cooperation with the movement of the trigger to allow the firing pin to move to a second position, wherein a firing pin handle is attached to the firing pin and extends through the slot in the housing.

2. The rivet applier of claim 1 wherein a stop is present within the applier barrel to stop the firing pin.

3. The rivet applier of claim 1 wherein the trigger is mechanically linked to a slider capable of moving a trigger spring that is positioned to engage one or more notches on the firing pin.

4. The rivet applier of claim 1 wherein additionally present is a handle extending from the housing.

5. The rivet applier of claim 1 wherein additionally present adjacent to the distal end of the applier barrel is a recessed circular groove.

6. A rivet applier comprising a housing with a horizontal axis, an applier barrel comprising a passage substantially aligned with the horizontal axis, and a firing mechanism comprising a trigger;

the applier barrel having a proximal opening, a distal opening and a slot, wherein the proximal end of the applier barrel is attached to the housing and aligned with the horizontal axis of the housing;

a loader which is slidably mounted within the passage of the applier barrel, the loader comprising a loader handle attached thereto and extending substantially perpendicular to the horizontal axis and a central passage;

a firing pin which extends through said housing and the central passage of the loader, the firing pin being biased to extend through the applier barrel to the proximal opening and being mechanically linked to the firing mechanism for restraining-the firing pin in a first position and being capable of releasing the firing pin in cooperation with the movement of the trigger to allow the firing pin to move to a second position, wherein there is present a handle attached to the firing pin and extending through the housing to allow the rivet applier to be placed in a cocked position without moving the loader.

7. A rivet applier comprising a housing with a horizontal axis, an applier barrel comprising a passage substantially aligned with the horizontal axis, and a firing mechanism comprising a trigger;

the applier barrel having a proximal opening, a distal opening and a slot, wherein the proximal end of the applier barrel is attached to the housing and aligned with the horizontal axis of the housing;

a loader which is slidably mounted within the passage of the applier barrel, the loader comprising a loader handle attached thereto and extending substantially perpendicular to the horizontal axis and a central passage;

a firing pin which extends through said housing and the central passage of the loader, the firing pin being biased to extend through the applier barrel to the proximal opening and being mechanically linked to the firing mechanism for restraining the firing pin in a first position and being capable of releasing the firing pin in cooperation with the movement of the trigger to allow the firing pin to move to a second position, wherein additionally present is a rivet clip assembly comprising a clip barrel and clip body; the clip barrel has distal end and proximal end; a clip barrel opening is present on the distal end of the clip barrel and a barrel groove adjacent to the proximal end; the clip barrel has a chamber that is aligned with the passage of the applier barrel and allows the slidable movement of the loader therein; the clip body is attached to the clip barrel and extends substantially perpendicular thereto and is in communication therewith by a clip slot; the clip body adapted to contain at least one rivet, which is supported by a clip guide and biased by a clip spring wherein the clip body is attached to the distal end of the applier barrel by a clip ring on the external surface of the clip barrel adjacent to the proximal end of the clip barrel.

8. The rivet applier of claim 7 wherein the rivet clip assembly may rotate 360 degrees.

9. The rivet applier of claim 7 wherein the clip barrel is tapered.

10. The rivet applier of claim 7 wherein the distal end of the clip barrel has at least one relief cut.

* * * * *